(12) United States Patent
Lo et al.

(10) Patent No.: US 7,547,282 B2
(45) Date of Patent: *Jun. 16, 2009

(54) ULTRASONIC MONITOR FOR MEASURING HEART AND PULSE RATES

(75) Inventors: Thomas Ying-Ching Lo, Fremont, CA (US); Tolentino Escorcio, Dublin, CA (US); Ron Jong Chang, Fremont, CA (US)

(73) Assignee: Salutron, Inc., Fremont, CA (US)

( * ) Notice: Subject to any disclaimer, the term of this patent is extended or adjusted under 35 U.S.C. 154(b) by 189 days.

This patent is subject to a terminal disclaimer.

(21) Appl. No.: 10/758,608

(22) Filed: Jan. 14, 2004

(65) Prior Publication Data

US 2004/0167409 A1 Aug. 26, 2004

Related U.S. Application Data

(63) Continuation-in-part of application No. 10/346,296, filed on Jan. 15, 2003, now Pat. No. 6,843,771.

(51) Int. Cl.
  *A61B 8/14* (2006.01)
(52) U.S. Cl. .............. 600/459; 600/437; 600/453; 600/443; 600/465
(58) Field of Classification Search .......... 600/437, 600/453, 459, 465, 443, 485
  See application file for complete search history.

(56) References Cited

U.S. PATENT DOCUMENTS

| | | | |
|---|---|---|---|
| 3,020,260 A | 2/1962 | Nelson | |
| 3,978,849 A | 9/1976 | Geneen | |
| 4,083,366 A | 4/1978 | Gombrich et al. | |
| 4,086,916 A | 5/1978 | Freeman et al. | |
| 4,122,427 A | 10/1978 | Karsh | |
| 4,163,447 A | 8/1979 | Orr | |
| 4,239,048 A | 12/1980 | Steuer | |
| 4,256,117 A | 3/1981 | Perica et al. | |
| 4,357,944 A | 11/1982 | Mauser et al. | |
| 4,369,284 A | 1/1983 | Chen et al. | |

(Continued)

FOREIGN PATENT DOCUMENTS

DE 3345739 7/1985

(Continued)

OTHER PUBLICATIONS

Aritomo et al., "A wrist-mounted activity and pulse recording system", Proc. of 1st Joint BMES/EMBS Conf. 2:693 (1999).

(Continued)

*Primary Examiner*—Long V Le
*Assistant Examiner*—John F Ramirez
(74) *Attorney, Agent, or Firm*—Vierra Magen Marcus & DeNiro LLP

(57) ABSTRACT

The invention provides an ultrasonic monitor for measuring pulse rate values in a living subject, including a module with at least one source of ultrasonic energy, a gel pad comprised of a polymer and from about 50 to about 95% by weight of an ultrasound conductive diluent, wherein the gel pad is positioned in direct contact between the module and the living subject; an ultrasonic energy detector and associated hardware and software for detecting, calculating and displaying a readout of the measured rate values.

40 Claims, 6 Drawing Sheets

U.S. PATENT DOCUMENTS

| | | | | |
|---|---|---|---|---|
| 4,413,629 | A * | 11/1983 | Durley, III | 600/453 |
| 4,556,066 | A * | 12/1985 | Semrow | 600/459 |
| 4,947,859 | A * | 8/1990 | Brewer et al. | 600/528 |
| 5,130,955 | A | 7/1992 | Luerker et al. | |
| 5,136,621 | A | 8/1992 | Mitchell et al. | |
| 5,197,489 | A | 3/1993 | Conlan | |
| 5,243,992 | A | 9/1993 | Eckerle et al. | |
| 5,265,614 | A | 11/1993 | Hayakawa et al. | |
| 5,309,916 | A | 5/1994 | Hatschek | |
| 5,318,035 | A * | 6/1994 | Konno et al. | 600/459 |
| 5,431,170 | A | 7/1995 | Mathews | |
| 5,474,072 | A | 12/1995 | Shmulewitz | |
| 5,494,038 | A | 2/1996 | Wang et al. | |
| 5,738,104 | A | 4/1998 | Lo et al. | |
| 5,782,767 | A * | 7/1998 | Pretlow, III | 600/443 |
| 5,795,300 | A | 8/1998 | Bryars | |
| 5,807,267 | A | 9/1998 | Bryars et al. | |
| 5,810,736 | A | 9/1998 | Pail | |
| 5,876,350 | A | 3/1999 | Lo et al. | |
| 5,941,837 | A | 8/1999 | Amano et al. | |
| 5,960,089 | A | 9/1999 | Bouricius et al. | |
| 6,039,694 | A | 3/2000 | Larson et al. | |
| 6,080,111 | A | 6/2000 | Pao-Lang | |
| 6,156,842 | A | 12/2000 | Hoenig et al. | |
| 6,302,848 | B1 | 10/2001 | Larson et al. | |
| 6,364,842 | B1 | 4/2002 | Amano et al. | |
| 6,371,920 | B1 * | 4/2002 | Kamimoto et al. | 600/481 |
| 6,394,960 | B1 | 5/2002 | Shinogi et al. | |
| 6,447,456 | B1 | 9/2002 | Tsubata | |
| 6,554,772 | B2 * | 4/2003 | Nakamura et al. | 600/459 |
| 6,584,660 | B1 | 7/2003 | Shimogawa et al. | |
| 6,623,435 | B2 | 9/2003 | Tsubata | |
| 6,716,169 | B2 | 4/2004 | Muramatsu et al. | |
| 6,744,178 | B2 | 6/2004 | Muramatsu et al. | |
| 6,758,816 | B1 | 7/2004 | Tsubata et al. | |
| 6,767,329 | B2 | 7/2004 | Amano et al. | |
| 6,843,771 | B2 * | 1/2005 | Lo et al. | 600/459 |
| 6,992,443 | B2 * | 1/2006 | Lin et al. | 313/582 |
| 2001/0033825 | A1 | 10/2001 | Douglas | |
| 2001/0034486 | A1 | 10/2001 | Larson et al. | |
| 2001/0039380 | A1 | 11/2001 | Larson et al. | |
| 2001/0056243 | A1 | 12/2001 | Ohsaki et al. | |
| 2002/0019586 | A1 | 2/2002 | Teller et al. | |
| 2002/0068871 | A1 * | 6/2002 | Mendlein et al. | 600/459 |
| 2002/0151810 | A1 | 10/2002 | Wong et al. | |
| 2006/0106311 | A1 * | 5/2006 | Lo et al. | 600/459 |

FOREIGN PATENT DOCUMENTS

| | | |
|---|---|---|
| EP | 0283854 | 9/1988 |
| EP | 0861045 B1 | 8/2002 |
| GB | 2036504 | 6/1980 |
| JP | 60-154793 | 8/1985 |
| WO | WO/97/17015 A1 | 5/1997 |

OTHER PUBLICATIONS

Dupuis et al, Combined Detection of Respiratory and Cardiac Rhythm Disorders by High-Resolution Differential Cuff Pressure Measurement, IEEE Transaction on Instrumentation & Measurement, 49:498-502 (2000).

Gagnadre et al., Fibre Optic Sensor for Physiological Parameters, Electronic Letters, 34:1991-1993 (1998).

Hertzman, "Photoelectric Piethysmography of the fingers and toes in man", Proceedings of the Society for Experimental Biology and Medicine 37:1622-1637 (1937).

Im et al, A Study for the Development of a Noninvasive Continuous Blood Pressure Measuring System by Analyzing Radial Artery Pulse from a Wrist, IEEE-EMBC & CMBEC, 2:1033-1034 (1995).

Tamura et al., The Design of an Ambulatory Physical Activity Monitor and It Application to the Daily Acitvity of the Elderly, IEEE-EMBC & CMBEC, 2:1033-1034 (1995).

Chinese Patent Appl. No. 200480007089.9 filed Jan. 14, 2004, Office Action dated Feb. 15, 2008.

European Office Action dated Sep. 22, 2008 in European Application No. 04702240.5.

Dow Corning Product Description.

Teknor Apex Product Description.

GLS Corporation Product Description.

Septon Product Description.

Kraton Product Description.

Gelest Product Description.

* cited by examiner

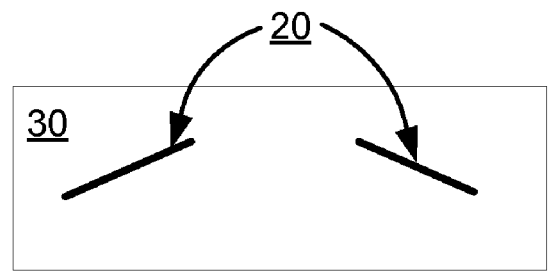
Figure 6A
Figure 6B
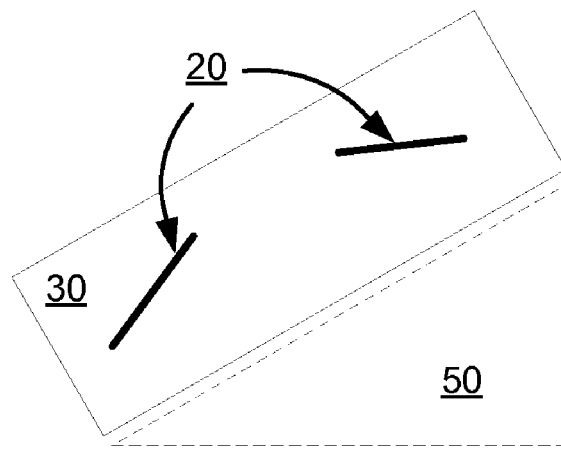
Figure 6C
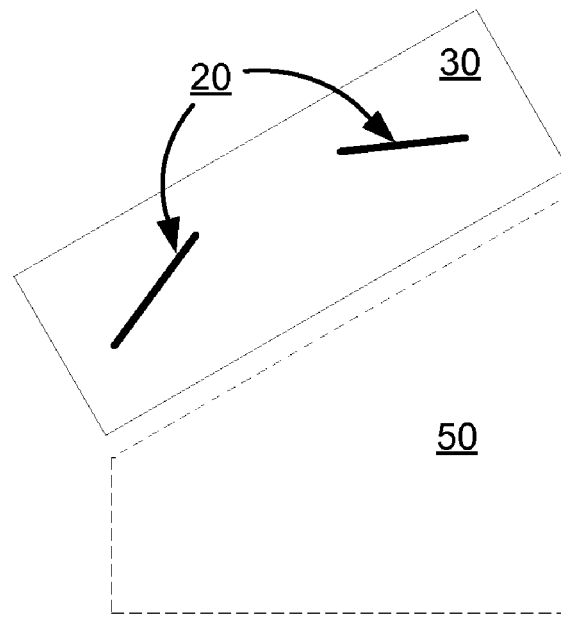

ULTRASONIC MONITOR FOR MEASURING HEART AND PULSE RATES

CROSS-REFERENCES TO RELATED APPLICATIONS

The instant nonprovisional application is a continuation-in-part of parent nonprovisional patent application Ser. No. 10/346,296, filed Jan. 15, 2003 and incorporated by reference herein for all purposes.

BACKGROUND OF THE INVENTION a) Field of the Invention

The present invention relates to ultrasonic monitors for measuring heart and pulse rates in living subjects. Methods for measuring heart and pulse rates of living subjects through ultrasonic means are also encompassed by the instant invention.

b) Description of Related Art

Measuring Heart and Pulse Rates

Measuring heart and pulse rates in living subjects has been accomplished by various means. The pulse rate is commonly measured by lightly touching one's fingers over an artery and counting the rate of pulsation. The heart rate is usually measured by a sensing device using electrodes that monitor the electrical activity of the heart (e.g., contact monitors) based on electrocardiograms (EKG OR ECG). Measuring rate values is a useful tool in individualizing and optimizing exercise regimens. Individuals who want to increase endurance or performance aim for certain target heart rates to maximize progression towards their goals. Conversely, adults with a history of heart disease must avoid exceeding a certain heart or pulse rate to reduce unnecessary strain on the heart and resultant injury.

The heart rate is the rate of contractions over a given time period, usually defined in beats per minute. A pulse can be defined as the rhythmical dilation of a vessel produced by the increased volume of blood forced into the vessel by the contraction of the heart. The pulse can be felt at many different points on the body, including the wrist (radial artery) and neck (carotid artery), which are among the most easily accessible points. Since a heart contraction almost always produces a volume of blood that can be measured as a pulse, the heart rate and pulse rate are usually the same. However, there are certain situations where the pulse rate may differ from the heart rate. For example, the body may generate an irregular heart beat or a premature heart beat. In this scenario, a heart contraction would not force out enough blood to be measured as a pulse and the measured pulse rate would be different from the heart rate.

Heart rate monitors that provide continuous heart rate readings rather than a single point measurement require wearing a chest strap. There are a few heart rate monitors that do not require a chest strap. Most, if not all, of these monitors do not provide continuous heart rate readings but measure the wearer's pulse and transmit that pulse upon request. Most users would have to stop exercising in order to get this type of measurement, which is disruptive to an exercise regimen. In U.S. Pat. Nos. 5,738,104 and 5,876,350 and European Patent No. 0861045B1, Lo et al disclosed an EKG heart rate monitor that does not require a chest strap so that the user does not have to stop exercising to take a heart rate measurement. All the sensors and electronics are contained in a wristwatch. The software is effective in filtering out muscle motion noise. Therefore the user can walk and jog while taking a single point measurement. However, this technology still does not offer continuous readings. Hence, most users or heart patients that demand continuous heart rate readings choose a monitor that requires a chest strap. Most of the population, including the elderly, would prefer a monitor that does not require a chest strap. There are also portable patient monitors (e.g., vital signs monitors, fetal monitors) that can perform functions as diverse as arrhythmia analysis, drug dose calculation ECG waveforms cascades, and others. However, such monitors are usually fairly large (e.g., size of a small TV) and are connected to the patient through specific wires. The art has, thus, a need for an improved heart monitoring device, specifically one that provides continuous heart rate readings for both healthy and compromised living subjects without the need for chest straps, wirings, or the like.

Since the advent of the wristwatch, the wrist has offered a convenient, accessible, and non-intrusive location for an individual to wear a mechanical device. Moreover, the shallow depth of the radial artery in the wrist offers a number of advantages for allowing the continuous detection of blood rate pulses. Many different sensor types for pulse detection in the wrist have previously been developed.

Im & Lessard, in "Proceedings of IEEE-EMBC & CMBEC", 2:1033-1034 (1995) and Tamura et al., in "Proceedings of IEEE-EMBC & CMBEC", 2:1591-1592 (1995) describe implementation. Pulse detection in heart rate measurement has been implemented by means of piezoelectric sensors where the mechanical stimulus generated by the pressure pulse is converted to an electrical signal for further signal processing.

Dupuis & Eugene, in "IEEE Transaction on Instrumentation & Measurement", 49:498-502 (2000) describe use of a strain gauge differential pressure sensor in a measurement system, where a low pressure cuff was wrapped around the wrist and then the pressure modulation in the cuff caused by the pressure pulse was measured with strain gauges.

Sorvoja H., in her Licentiate Thesis, University of Oulu (1998—in Finnish) and Ruha et al., in Proceedings of Biosignal 1:198-200 (1996) describe utilization of new pressure sensitive materials like electromechanical film (EFMi) and polyvinylidene fluoride (PVDF) in sensors for pulse detection in the radial artery Gagnadre et al., in Electronic Letters, 32:1991-1993 (1998) describes the use of fiber optic sensors to detect heart rate. A multimode optical fiber was placed between two aluminum plates. The force generated by the pressure pulse caused variation in the modal distribution in the fiber and the pulse is detected using a photodetector.

Infrared optical sensors in cardiovascular pulse detection typically measure the optical power variation which is due to absorption or scattering when the amount of blood in the measurement volume varies. This kind of measurement, known as photo-plethysmography (PPG), was first disclosed by Herztman, "Photoelectric Plethysmography of the fingers and toes in man", Proceedings of the Society for Experimental Biology and Medicine 37:1622-1637 (1937).

PPG is mainly used for measuring pulsation in a capillary network. Workers such as Hast, "Optical heart rate detection structures & methods. Thesis for the Diploma Engineer Degree", University of Oulo (Finnish), and Aritomo et al., "A wrist-mounted activity and pulse recording system", Proc. of 1st Joint BMES/EMBS Conf. 2:693 (1999), have applied PPG to measurements above the radial artery.

Sensors that monitor pressure pulses in the wrist such as mentioned above suffer a common problem. The pressure pulses are generally attenuated by the tissues between the artery and the sensor such that much of the high frequency components in the signal are lost. When the subject is in motion, muscle movement may create substantial noise at the pressure sensors. These noise signals are low frequency in nature. They will thus make it very difficult to identify blood pressure pulses reliably. Photo-plethysmography (PPG) suffers similar problem that when the interface between the photo detector and the wrist is not stable due to motion, the intensity of the transmitted or reflected light signal may be significantly disturbed.

The ambient lighting condition also plays an important role to the effectiveness of PPG technology. The various different technologies using strain gauge, piezoelectric film material, infrared optical coupler pair and fiber optic sensor can only measure heart rate with reasonable reliability when the subject is still. They are not practical for sports, fitness and rehabilitation applications where the subject is moving.

It is well known in the prior art to employ sonar technology to identify moving objects. A piezoelectric crystal may be used both as the power generator and the signal detector. In this case, the ultrasonic energy is emitted in a pulsed mode. The reflected signal is picked up by the same crystal after the output power source is turned off. The time required to receive the reflected signal depends upon the distance between the source and the object. The frequency shift, better known as Doppler shift, is dependent upon the speed of the moving object. This technique requires only one crystal but the detector circuit will only work after the transmitter power is turned off. It is conceivable to use this method to detect the motion of a blood vessel wall to extract the pulse rate information. However, for superficial blood vessels this technique requires very high speed power switching due to the short distance between source and object. In addition, muscle movement will also generate reflections that compromise the signal-to-noise-ratio in the system. The muscle noise signal in this case is very similar to the signal due to blood vessel wall motion. Therefore, it is very difficult to detect heart rate this way when the living subject is in motion. The advantage of this approach, however, is low cost and low power consumption. For continuous mode two piezoelectric elements may be used. Either may be used as the transmitter and the other as receiver or detector at a given time. These two elements can be positioned at an angle to the direction of the flow on opposite sides or on the same side of the conduit. If they are on the same side, the two crystals can be conveniently packaged into a module. The flow rate or flow velocity is proportional to the Doppler shift relative to the operating frequency. The main advantage of continuous mode for pulse rate application is that the Doppler shift due to blood flow is distinctly different from the shifts due to muscle artifacts or tissue movement. The shift due to blood flow is higher in frequency than that due to muscle motion. Therefore, even if the muscle motion induced signals are larger in amplitude, they may still be filtered out by a high pass filter in either analog or digital form to retain the blood flow signals. In this respect the ultrasound method is superior to infrared, pressure sensing and even EKG based technologies.

One device useful for the measurement of heart and pulse rates is an electronic unit worn on the wrist. Several such devices are known in the art. U.S. Pat. No. 4,086,916 (Freeman et al.) discloses a cardiac wristwatch monitor having ultrasonic transducers mounted in the wrist strap portion. The transducers are encased in an epoxy and covered with an insulative coating. U.S. Pat. No. 4,163,447 (Orr) discloses a wrist-mounted heartbeat rate monitor that relies upon light-emitting diodes. U.S. Pat. No. 4,256,117 (Perica et al.) discloses a wrist-mounted combination stopwatch and cardiac monitor that uses a pressure transducer to measure pulse rate.

In Freeman's invention, a wristwatch was intended to offer a continuous pulse rate monitor. However, ultrasonic energy is prone to diffraction and attenuation at the interface of two media of different densities. Any air gap at the interface or any air bubbles in the media will also make ultrasonic energy transfer unreliable. Therefore, it has been a standard practice to apply water or an aqueous gel between the transducer module and the living subject to eliminate any air gap. Unfortunately water and aqueous gels dry up quickly in open air. For continuous rate monitoring, the requirement to apply water or gel frequently is not acceptable. In U.S. Pat. Nos. 6,371,920 B1 and 6,394,960 B1 attempts were made to overcome this problem by using an array of small transducers protruding from the support surface to make firm contact with a living subject with no air gap in between. However, this increases the complexity and cost of the transducer device and its driving electronics significantly. The air gap will not be totally removed, either, due to body hairs and the variable condition of skin from person to person. In U.S. Pat. No. 6,447,456 B1, two sets of transducers are used at the radial artery and the ulnar artery. The idea is to cope with the compromised signal quality due to motion at the wrist that may create an air gap from time to time. With two sets of transducers the hope is that at least one of them will reliably detect the Doppler signal to identify the heart beat. The disadvantages of continuous mode over pulsed mode are higher cost and more power consumption.

BRIEF SUMMARY OF THE INVENTION

The present invention relates to an ultrasonic monitor for measuring rate values of a living subject, including heart rate and pulse rate. Due to continued advances in piezoelectric material and microelectronic technologies, an ultrasound based pulse rate monitor system can be miniaturized to reduce cost and power consumption.

One aspect of the invention provides an ultrasonic monitor for measuring pulse rate values in a living subject, including a module with at least one source of ultrasonic energy, a gel pad comprised of a polymer and from about 50 to about 95% by weight of an ultrasound conductive diluent, wherein the gel pad is positioned in direct contact between the module and the living subject; an ultrasonic energy detector and associated hardware and software for detecting, calculating and displaying a readout of the measured rate values. The gel pad is made of a polymer having the following characteristics:

a) Hardness: Needle Penetration from about 5 to about 300 ($\frac{1}{10}$ mm) according to ASTM D15, preferably from about 25 to about 150, and most preferably from about 30 to about 50;

b) Tensile Strength from about 5 to about 500 psi according to ASTM D412, preferably from about 10 to about 300 psi, and most preferably from about 50 to about 200 psi; and c) Elongation from about 50% to about 800% according to ASTM D412, preferably from about 200% to about 700%, and most preferably from about 300% to about 500%.

The gels are stable after stress and temperature cycling (with no oil exuding out). The display may optionally include electronics and software for analyzing the rate values from a living subject. Conversely, the module may include the electronics and software for analysis of the rate values.

Another aspect of the invention provides a method of measuring rate values of a living subject. The method includes providing an ultrasonic monitor as described above and contacting the monitor with the living subject.

BRIEF DESCRIPTION OF THE DRAWINGS

The present invention is best understood when read in conjunction with the accompanying figures which serve to illustrate the preferred embodiments. It is understood, however, that the invention is not limited to the specific embodiments disclosed in the figures.

FIGS. 6A-C show depicts a few possible shapes of gel pads designed for a given bias angle and a given focal depth.

DETAILED DESCRIPTION OF THE INVENTION a) Definitions and General Parameters

The following definitions are set forth to illustrate and define the meaning and scope of the various terms used to describe the invention herein.

The terms "ultrasonic" and "ultrasound" are used interchangeably herein and refer to a sound wave having a frequency between about 30 KHz and about 30 MHz. An "ultrasonic transducer" (i.e., a transducing means) is a device used to introduce sonic energy into a test object (e.g., living subject) and also to detect reflected energy from the object as in the instant invention. Typical of this type of device are piezoelectric crystals which respond to electric pulses from an instrument with a mechanical pulse, and to mechanical pulses (reflected energy) from the test object with electrical energy detectable by the instrument. Ultrasound may also be used as a sound wave imaging technique used to examine a part of the body (e.g., breast, abdomen, heart) in order to evaluate a specific tissue or progression of a diseased tissue. In addition, ultrasound is used to monitor fetuses and their growth.

A "rate value" as used herein, refers to a value that can be measured. A rate value of the instant invention includes, but is not limited to, a heart rate, pulse rate, fetal heart rate, and fetal pulse rate.

Figure 2:
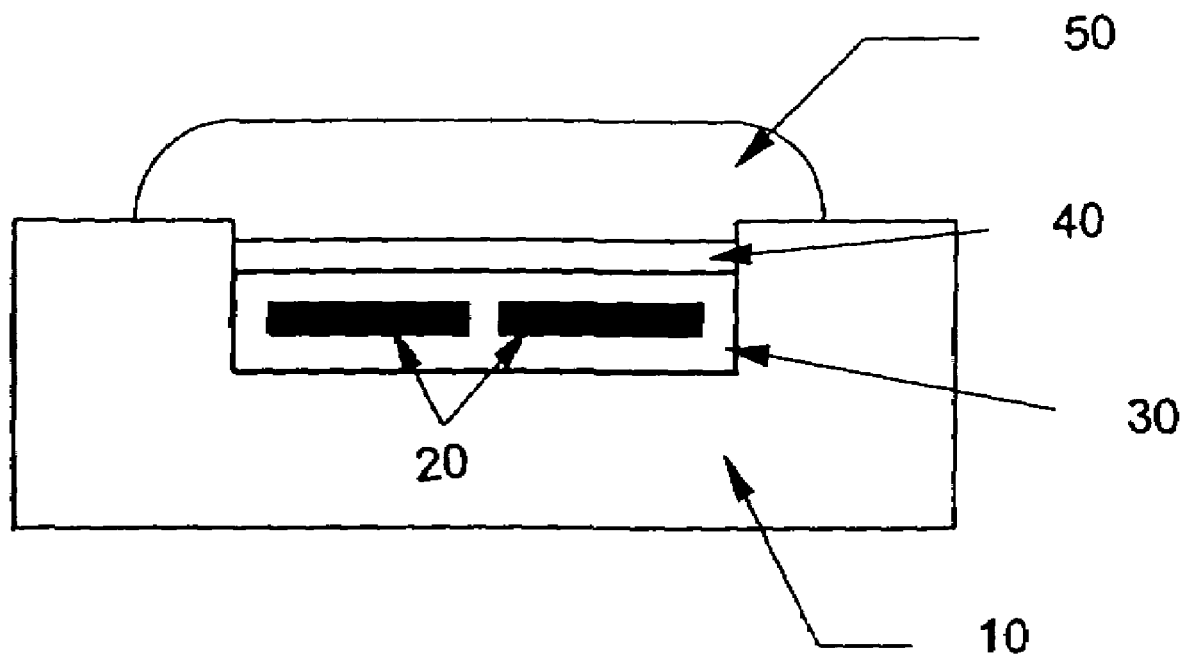
FIG. 2 depicts a cross sectional view of a transducer module assembly. The substrate of the housing (10) may be metal or plastic. The transducers (20) are molded in ABS and permanently adhered to the housing. On top of the transducer module (30), there is an optional thin adhesive layer (40) which can be a lower oil content gel or an appropriate adhesive material. The top structure is the gel pad (50) that is in direct contact with the living subject.
Figure 3:
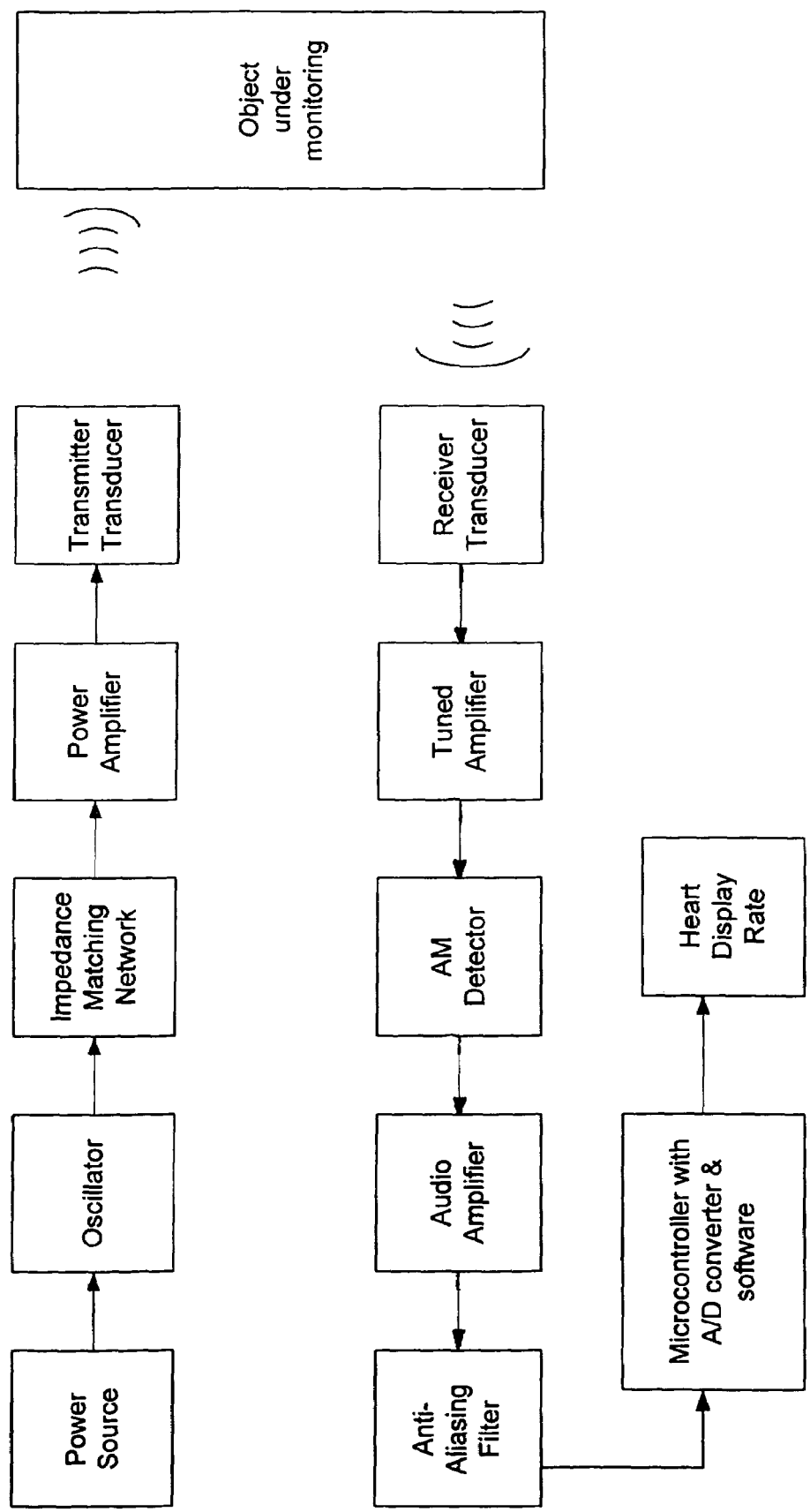
FIG. 3 depicts a block diagram of a typical ultrasound based heart rate monitor system.
Figure 4:
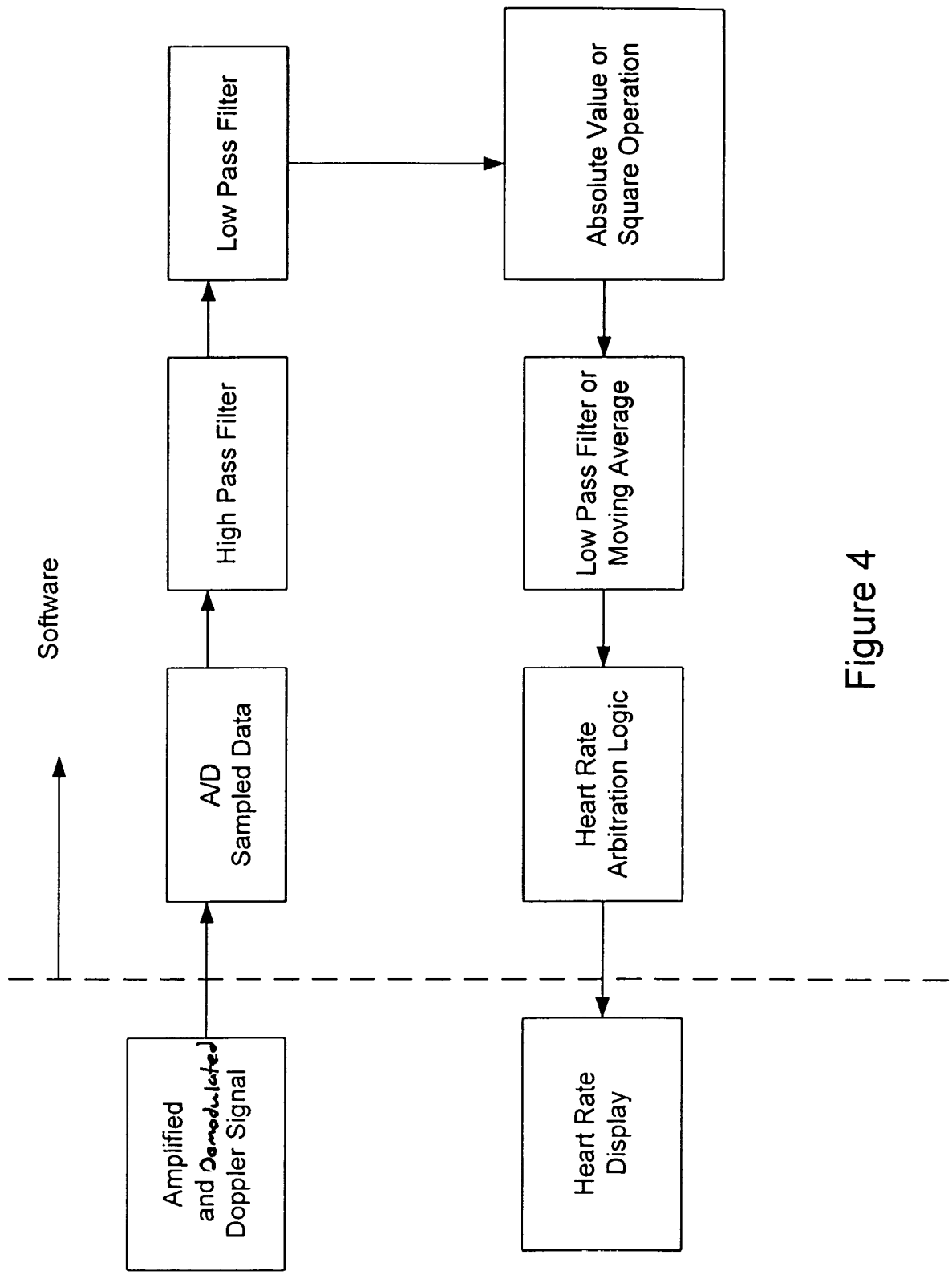
FIG. 4 depicts the block diagram of the software of this invention. The amplified Doppler signal after anti-aliasing filtering is sampled by an A/D converter in a microcontroller. The sampled data is further digitally filtered by a high pass filter or a combination of high pass and low pass filters. The output is applied with either an absolute value operator or a square operator followed by a stage of low pass filter. Finally this digitally processed data is used to determine the pulse rate.

The term "module with transducing means" refers to the assembly that contains the piezoelectric transducer. See, for example, FIG. 2. The module may optionally include electronics for analysis of the rate values.

The term "thermoset gel" as used herein refers to a gel that is generally made of a chemically bonded three-dimensional elastomeric network which entraps a large amount of low volatility liquids or diluents. The elastomeric network is permanent and cannot be reversed to a liquid state through heating. A certain amount of diluent is necessary in order to ensure good conformability of the gel to the skin and low attenuation for ultrasound transmission while still maintaining the load bearing properties. The gel can be used at a temperature that ranges from −30° C. to +70° C., wherein the gel maintains its shape and load-bearing elastic properties. A "silicone gel" or a "polyurethane gel" is an example of a thermoset gel. Prior to this invention, thermoset gels have not been used as ultrasound transmission media.

The term "thermoplastic gel" as used herein refers to a gel that is generally made of a thermoplastic elastomer with a large proportion of interdispersed diluent. Thermoplastic elastomers include block copolymers such as styrene-butadiene-styrene, styrene-isoprene-styrene, styrene/ethylene-co-butylenes/styrene, and styrene/ethylene-co-propylene/styrene. The styrene end blocks form glassy domains at room temperature. The glassy domains act as physical crosslinks that provide the elastomeric properties of the polymer. During heating above the glass transition temperature of styrene, i.e., about 100° C., the glassy domains melt and the polymers revert to a liquid state. During cooling, the glassy domains re-form again. Hence, the process is reversible. Other block copolymers, such as ethylene-(ethylene-co-butylene)-ethylene copolymers which contains crystalline polyethylene end blocks, can also be used to prepare thermoplastic gels. Prior to this invention, thermoplastic gels have not been used as ultrasound transmission media.

b) The Ultrasonic Monitor

One aspect of the invention provides an ultrasonic monitor for measuring pulse rate values in a living subject, including a module with at least one source of ultrasonic energy (transducer), a gel pad comprised of a polymer and a mineral oil, wherein the gel pad is positioned in direct contact between the module and the living subject; an ultrasonic energy detector and associated hardware and software for detecting, calculating and displaying a readout of the measured rate values. The gel pad is made of a polymer having the following characteristics:

a) Hardness: Needle Penetration from about 5 to about 300 (1/10 mm) according to ASTM D15, preferably from about 25 to about 150, and most preferably from about 30 to about 50;

b) Tensile Strength from about 5 to about 500 psi according to ASTM D412, preferably from about 10 to about 300 psi, and most preferably from about 50 to about 200 psi; and c) Elongation from about 50% to about 800% according to ASTM D412, preferably from about 200% to about 700%, and most preferably from about 300% to about 500%.

In a preferred embodiment of the invention, the monitor is a wristwatch with attached wristband, wherein the module is attached to the wristband. In another preferred embodiment the transducer includes a first and a second piezoelectric crystal, wherein the crystals are positioned at an angle to each other, and wherein the angle is determined based on the distance of the transducer to the living subject. The first piezoelectric crystal is energized by an original ultrasonic frequency signal, wherein the original ultrasonic frequency signal is reflected off the living subject and received by the second piezoelectric crystal. More specifically, the module includes a pair of piezoelectric crystals at an angle to each other, wherein the angle is determined by the depth of the object being monitored. If the object is a fetus deep inside a womb, the two crystals are placed parallel to each other. If the object is the radial artery of a human subject (e.g., adult, infant), the angle of the two crystals with respect to the direction of the blood flow would be about 0 to about 60. One of the crystals is energized at an ultrasonic frequency. The signal is then reflected back by the living subject and picked up by the second crystal. The frequency received is either higher or lower than the original frequency depending upon the direction and the speed of the fluidic mass flow. For example, when blood flow is monitored, the direction of flow is fixed. Thus, the Doppler frequency which is the difference between the original and the reflected frequency depends only upon the speed of the blood flow.

The ultrasonic monitor includes an ultrasonic frequency driver, an AM or FM detector, an amplifier, filter circuits and a microcontroller. The driver circuit is composed of an oscillator running at a frequency between about 30 KHz to about 30 MHz, an impedance matching network and a Class C power amplifier. Ultrasonic energy is delivered to one of the two piezoelectric elements in the module by the power amplifier. The other element picks up the reflected ultrasonic signal. This signal is amplified and then amplitude demodulated (AM) or frequency demodulated (FM) to yield the Doppler frequencies. The Doppler frequencies in audio range are further amplified and filtered to avoid aliasing before they are digitally sampled and processed by a microcontroller with built-in analog-to-digital converter and software. The software digitally filters out the noise signals due to muscle artifacts by a high pass filter with a 3-db corner frequency at about 10 to about 1500 Hz depending on the original ultrasound operating frequency. Following that, a square operation and a low pass filter will further condition the signal appropriately for heart rate arbitration. The 3-db corner frequency of the low pass filter is about 500 to about 5000 Hz depending upon the original ultrasound operating frequency. The heart rate arbitration logic in the prior art of Lo et al. may be applied to this invention with minor modifications.

The module may optionally include electronics and software for analyzing the rate values of the living subject, such as heart rate or pulse rate. Alternatively, the display unit may include the electronics and software for analyzing the rate values. As such, there are at least two alternative embodiments with respect to the wrist watch ultrasonic monitor.

In one embodiment of the invention, the transducers, the electronics and the software are all housed in the same module. The module is mechanically attached to the wrist band and it may be positioned at the radial artery of a living subject. The gel pad faces the wrist of the living subject and is held in place by the wrist band. The two crystals (supra) are located in the interior of the module right behind the gel pad. The measured blood flow and/or heart rate values can be sent to the watch display unit via wireless means. In this case, the module has a transmitter circuit and the display unit has a receiver circuit. The carrier frequency may be chosen based upon conventionally used frequencies, e.g. 5 KHz, 120 KHz, 455 KHz, 433 MHz, 900 MHz, etc. These frequencies are used in various chest strap heart rate monitors. Currently, the most popular frequency used is 5 KHz. Therefore, the module with all the electronics and software included may be offered as a direct replacement to the existing chest strap products in the market. The display unit in this case is the wristwatch with wireless receiver circuit built-in. Optionally, the module can be fastened separately on its own strap adapted to fit another part of the living subject where blood flow can be conveniently monitored. This is the preferred approach since the battery compartment in the module may be designed to allow users to replace the battery with ease. The frequency of use and the length of time per use determine how frequently the battery needs to be replaced for a given type of battery.

Figure 1A:
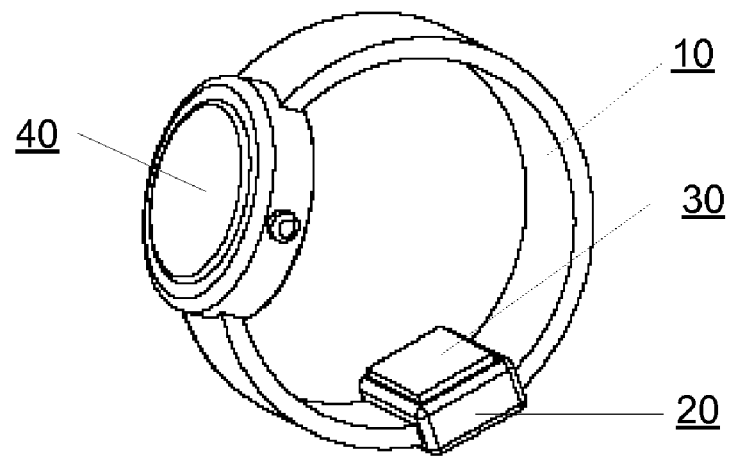
FIG. 1A depicts a front view of an ultrasonic monitor of the instant invention. Shown here is a wristwatch with attached wristband (10) having a module (20) with a gel pad (30), wherein the gel pad contacts the skin of a living subject. The figure also depicts the display unit (40) which provides a readout of measured rate values.

In another embodiment of the invention (shown in FIG. 1A), the same electronics and software are placed within the watch display unit while the transducers and gel pad are housed within the module. Connecting wires are molded into the wrist band to connect to the ultrasound driving circuit. In this case, a high energy density battery is required to reduce the frequency of battery change. Alternatively, a rechargeable battery may be employed. The battery will be charged wirelessly so that the watch unit is waterproof for swimmers and divers. As battery technology continues to improve in energy density and lifetime, this integrated approach may eventually be preferred. In another embodiment, the monitor may be held in place by or integrated into a head band for monitoring temporo pulses.

Figure 1B:
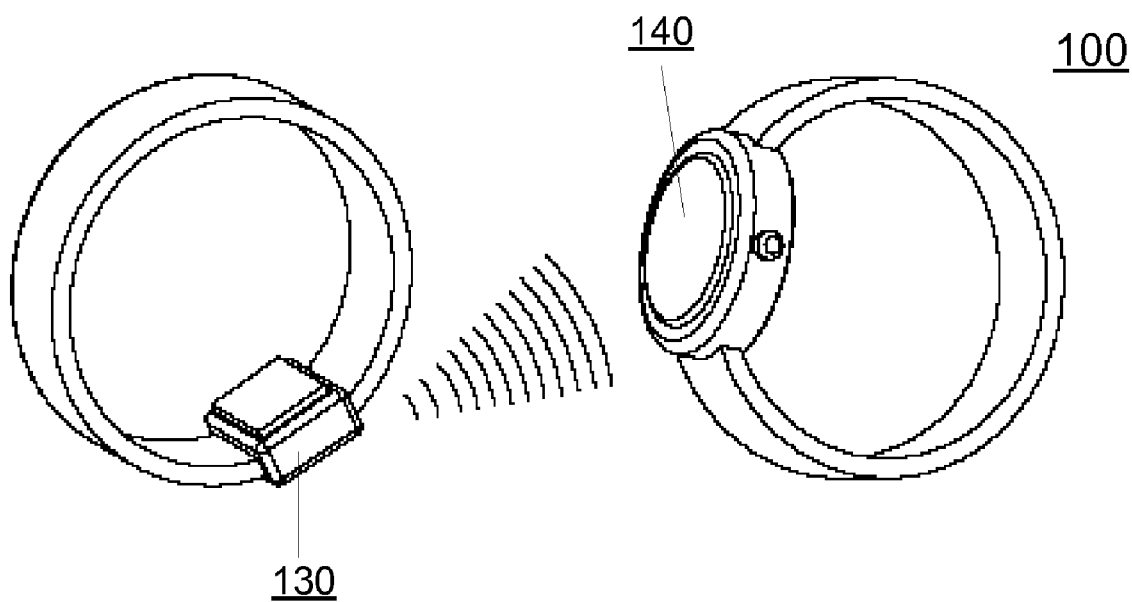
FIG. 1B depicts a front view of an alternative embodiment of an ultrasonic monitor in accordance with the present invention.

In still other embodiments in accordance with the present invention, for example embodiment 100 of FIG. 1B, the transducers and gel pad are housed within a first module 130 proximate to a first portion of the subject (i.e. the wrist of one hand), while the electronics and software and watch display unit are present within a second, separate module 140 secured to another part of the subject (i.e. the wrist of the other hand). The first (sensing) module may send sensed information to the second (processing/display) module through a wireless (preferred) or wired communication medium. In accordance with still other embodiments of the present invention, the position of the various processing functions may be allocated in any manner between sensing and display modules in different locations, for example on different wrists as shown in the specific embodiment of FIG. 1B.

Examples of rate values that can be measured with the ultrasonic monitor include, but are not limited to, heart rate values and blood pulse rate values. Such rate values can be obtained from human adults, infants, and fetuses or from other animals.

c) Polymers and Gels

The ultrasonic monitor includes a gel pad which is positioned in direct contact with the module and the living subject. Ultrasound energy does not propagate efficiently through air, thus a couplant (gel pad) is needed for efficient transmission between the transducer and the living subject. Gels in fluidic state may be used as couplants, however, such fluidic gels are likely to dry up quickly due to being water based. Hence, the instant invention preferably employs oil based gels in solid form to achieve efficient transmission between the transducer and the object. As such, the gel pad is made of a specific polymer which is used to conduct ultrasound waves such that the waves can be converted to measurable rate values. In a preferred embodiment, the polymer is a thermoset or thermoplastic gel. The gel of the present invention may include any elastomer type, elastomer molecular weight, crosslinking density, percentage of diluents, and the like. The gel pad may be about one square centimeter in size and its shape may be square, rectangular or round. Examples of thermoset gels include, but are not limited to, silicone or polyurethane gels. Silicone gels can be based on the reaction between a vinyl terminated polydimethylsiloxane, polymethylphenylsiloxane, or polydiphenylsilocaxane, and a hydride terminated polydimethylsiloxane, polymethylphenylsiloxane, or polydiphenylsiloxane. Polyurethane gels can be based upon the reaction of polybutadienediol, polybutadienetriol, poly(ethylene-co-propylene)diol, poly(tetraethylene oxide)diol, poly(ethylene oxide)diol, or castor oil with polyisocyanates such as toluene diisocyanate, or methylene diisocyanates. Examples of thermoplastic gels include, but are not limited to, styrene-(ethylene-co-butylene)-styrene, styrene-(ethylene-co-propylene)-styrene, styrene-butadiene-styrene, styrene-isoprene-styrene ethylene-(ethylene-co-butylene)-ethylene and other elastomeric block copolymers.

The term "gel" is often used to describe a wide variety of materials which may have different properties. The art generally distinguishes three types of gels: thickened fluids, hydrogels, and stable soft elastomeric gels. Examples of thickened fluids are toothpastes, dishwasher detergents, and the like. These fluids are typically thickened by fumed silica, bentonite clay, or other inorganic thickening agents. Upon gentle shaking or squeezing, this type of gel flows readily in a liquid-like fashion. However, this gel cannot recover its original thickened shape. Such gels are, thus, not suitable for applications where the gel needs to take on a specific shape or form.

Hydrogels typically include water soluble, high molecular weight polymers such as poly(vinyl alcohol), polyacrylamide, poly(acrylic acid), and the like. Hydrogels also contain a high percentage of water or water compatible fluids such as glycol. Hence, hydrogels can be characterized as water-like fluids or water compatible fluids, thickened by a high molecular weight organic polymer. Furthermore, this type of gel, depending on the composition, can be a fluid or elastic solid. If a lower molecular weight water soluble polymer and/or a high percentage of water is used, a fluid-like hydrogel is formed. A fluid-like hydrogel such as AQUASONIC™ hydrogel is widely used as a medium for ultrasonic transmission. In fact, there are several commercial gel products used for ultrasonic transmission, often simply referred to as ultrasound gel or ultrasound transmission gel. U.S. Pat. Nos. 6,328,695; 6,251,076; and 6,159,149 refer to the use of a gel as transmission medium with respect to their patented ultrasonic devices. If a high molecular weight water soluble polymer and/or a low percentage of water is used, the gel can form a soft elastic solid which is capable of carrying a moderate level of mechanical stress. The elasticity is derived from the temporary network formed by hydrogen bonding of water molecules to the polar groups of the polymers. U.S. Pat. Nos. 5,265,614 and 5,078,149 as well as JP Patent Nos. 59-49750 and 59-82838 describe the use of such gels based on poly (vinyl alcohol). However, since all these fluids and gels are volatile, they tend to evaporate even at room temperature and need to be kept in a closed environment (e.g., container, vacuum). Although these fluids and gels may possess load-bearing elastic properties for a short period of time, they are not stable upon long term exposure to the environment. At elevated temperature such as 40° C. and higher, the evaporation rate consistently increases, thereby further shortening the usefulness of the product. Furthermore, water freezes at 0° C., making this type of gel or fluid unsuitable for subzero temperatures. Consequently, hydrogels are only useful as ultrasound transmission media for a limited application, i.e., where the application does not require the gel to last beyond a short period of time.

When the application requires a gel that can be used for days or longer, stable soft elastomeric gel types are required. The elastomeric gels contain an elastomeric network with a high percentage of diluents which are generally nonvolatile at ambient temperatures. They possess elastic and load bearing properties at ambient conditions for a prolonged period of exposure (e.g., several month to a few years). They are stable and maintain elastic properties over a wide temperature range, i.e., from subzero temperatures to 70° C. The art distinguishes two categories of stable soft elastomeric gels: thermoset gels and thermoplastic gels. Thermoset gels are made of a chemically bonded three-dimensional elastomeric network which entraps a large amount of low volatility liquids or diluents. The elastomeric network is permanent and cannot be reversed to a liquid state through heating. A certain amount of diluent is necessary in order to ensure good conformability of the gel to the skin and low attenuation for ultrasound transmission while still maintaining the load bearing properties. In the absence of the required amount of diluent, the gel would resemble common rubber or elastomer which generally have a hardness of greater than 15 Shore A (ASTM D2240). For example, U.S. Pat. No. 4,901,729 describes the use of peroxide crosslinked polybutadiene, sulfur crosslinked polybutadiene, and silicone rubber as ultrasound propagation media. Examples of thermoset gels are silicone gels and polyurethane gels.

The elastomeric network of a silicone gel is formed by silicone rubber which is typically cured by reacting a hydride silicone rubber with a vinyl silicone rubber in the presence of a platinum catalyst. Both silicone rubbers are highly diluted with a non-reactive, low volatility silicone fluid prior to the reaction. The reaction can be carried out at 110° C.-120° C. for 30 minutes, or at room temperature for 48 hours. The silicone gels can also be made by using a silane terminated silicone elastomer which can be cured by exposure to ambient moisture. At the end of the reaction, the final composition contains about 5-45% silicone rubbers and 95-55% silicone fluid. A typical silicone gel composition is exemplified in U.S. Pat. No. 3,020,260, which is incorporated by reference herein. Some commercially available silicone gels include Dow Corning DC 3-4150, DC 3-4154, and Q3-6575; Sylgard 527; Gelest Gel D200 and D300; and P065 2-part and F065 one-part. Other silicone gel suppliers include General Electric Silicones of USA, Wacker Chemie of Germany, Shin-Etsu of Japan, and others. Silicone gels have been used for filled prosthesis devices as described in U.S. Pat. No. 4,455, 691 and as sealants as described in U.S. Pat. Nos. 5,290,826 and 5,245,980. U.S. Pat. Nos. 5,747,694 and 5,900,554 and their foreign equivalent, JP Patent No. 9043076, describe the use of a silicone gel in sealing a pressure sensor. U.S. Pat. No. 5,457,352 describes the use of a silicone elastomer applied during the gel phase of the adaptation layer in an ultrasonic converter, wherein the composition contains a large proportion of high density metal oxide for damping or blocking the ultrasonic wave.

The elastomeric network of a polyurethane gel is formed by reacting an isocyanate terminated rubber or oligomers (e.g., polybutadiene, polyisoprene, polytetrahydrofuran, or dimmer acid) with a hydroxyl terminated rubber or oligomers (e.g., polybutadiene, polyisoprenee, ethylene-butylene rubber, ethylene-propylene rubber, castor oil, or the like). Each rubber or oligomer is highly diluted with a nonvolatile and compatible diluent prior to the reaction. The diluents include mineral oils, vegetable oils, dibutyl phthalate, dioctyl phthalate, polybutenes, paraffinic oils, naphthenic oils, and the like. The final composition contains about 5-45% reactive rubbers and 95-55% total diluents. A typical polyurethane gel is described in U.S. Pat. Nos. 5,083,940; 4,982,054 and 4,962, 286, which disclose the use of polyurethane gels as sealant in electrical or telecommunication junction boxes. GB Patent No. 2,036,504 teaches the use of polyurethane rubber with International Rubber Hardness Degree (IRHD) of 15-50.

A thermoplastic gel is generally made of a thermoplastic elastomer with a large proportion of interdispersed diluent. Thermoplastic elastomers include block copolymers such as styrene-butadiene-styrene, styrene-isoprene-styrene, styrene/ethylene-co-butylenes/styrene (e.g., Kraton polymers by Kraton Inc). Other commercially available block copolymers include Septon polymers, which are styrene/ethylene-co-propylene/styrene (e.g., by Kuraray of Japan). In both, Kraton and Septon polymers, the styrene end blocks form glassy domains at room temperature. The glassy domains act as physical crosslinks that provide the elastomeric properties of the polymer. During heating above the glassy transition temperature of styrene, i.e., about 100° C., the glassy domains melt and the polymers reverse to a liquid state. During cooling, the glassy domains re-form again. Hence, the process is reversible, unlike that in the thermoset gels. Other block copolymers, such as ethylene-(ethylene-co-butylene)-ethylene copolymers which contains crystalline polyethylene end blocks, can also be used to prepare thermoplastic gels. The crystalline end blocks form crystallites which act as physical crosslinks to give elastomeric properties, rather than glassy domains as in the styrene based block copolymers. During heating, the crystallites melt and revert to the liquid state. During cooling, the crystallites re-form again. Similarly, the process is reversible.

In order to form a gel with thermoplastic elastomers, a large amount of low volatility diluent (e.g., typically 65-95% diluent) is used together with 5-35% block copolymers. The block copolymer may be a styrene/ethylene-co-butylene/styrene block copolymer with a total molecular weight of 30,000 to 300,000. The molecular weight of each styrene block may range from 4,000 to 35,000, and the molecular weight of the ethylene-co-butylene may range from 22,000 to 230,000. The weight percentage of the glassy polystyrene blocks is typically 20-40%, wherein the remaining 60-80% includes the center ethylene-co-butylene elastomer block. The suitable diluents include mineral oil, paraffinic oil, naphthenic oil, polybutenes, and the like, so long as they are compatible with the rubbery center portion of the block copolymers. Examples of gel composition based on block copolymers are described in U.S. Pat. Nos. 4,369,284 and 4,618,213, incorporated by reference herein. U.S. Pat. No. 4,618,213 describes the use of gels as toys or as acoustic isolators for noise reduction. U.S. Pat. Nos. 5,994,446; 5,925,707; and 5,710,206 describe thermoplastic gels for sealing applications. U.S. Pat. Nos. 6,406,499; 5,985,383; 5,925,707; 5,830,237; and 5,766,704, describe the use of thermoplastic gels for cushioning or shoe sole applications. U.S. Pat. Nos. 6,066,329 and 5,879,694 teach the use of thermoplastic gels for making transparent candles. U.S. Pat. No. 5,830,136 teaches the use of thermoplastic elastomer gel in optical sensors. All patents and publications are incorporated by reference herein.

Both thermoplastic and thermoset gels may be used in the instant invention. The gels used herein are generally defined by the following properties:

(i) Hardness: 5<Needle Penetration<300 (1/10 mm) according to ASTM D15, preferably 25<Needle Penetration<150, and most preferably 30<Needle Penetration<50.

(ii) Strength: 5<Tensile Strength<500 psi (pounds per square inch) according to ASTM D412, preferably from 10 to 300 psi, and most preferably from 50 to 200 psi.

(iii) Elongation: 50%<Elongation<800% according to ASTM D412, preferably from 200% to 700%, and most preferably from 300% to 500%.

(iv) Stability: The gels are stable after a stress and temperature cycling (with no oil exuding out).

The gels have good adhesion to the plastic housing of the ultrasonic transducer. The plastic housing may include acrylonitrile-butadiene-styrene (ABS), polycarbonate, nylon, and the like. Preferably, the gels are bonded to the plastic housing to form an integral unit. However, the instant invention also encompasses alternative ways to attach gels to the ultrasonic transducer.

In a preferred embodiment of the invention, a thermoplastic gel is over-molded, i.e., directly molded onto the plastic housing of a transducer (including a piezoelectric acoustic actuator and sensor), wherein specific molding techniques are employed. Such techniques are well known in the plastic industry. For example, the plastic encased ultrasonic transducer may be inserted into a mold, wherein a thermoplastic gel is heated to the molten state and injected into the mold by using an injection molding machine. The injection time and temperature of the gel are monitored to prevent damage to the transducer itself. In its molten state, the gel readily flows and eventually adheres to the plastic housing of the ultrasonic transducer (i.e., without using an additional adhesive at the interface between the plastic and the gel). However, in order to ensure a durable bond, it is preferable to apply a thin layer of primer or adhesive onto the surface of the plastic housing before the gel is molded onto it. One such suitable adhesive is a thermoplastic gel which has a lower oil content than the gel to be molded via injection. Several such lower oil containing thermoplastic gels are commercially available, such as Versaflex OM 6000 supplied by GLS Corporation and Monprene supplied by Teknor Apex Corporation. The extra layer of primer or adhesive functions as a tie-layer between the plastic housing of the transducer and the acoustic transmission gel. The plastic housing can be ABS, polycarbonate or nylon. The surface of the plastic housing is usually cleaned prior to applying the thin layer of primer or adhesive (e.g., with a solvent to remove mold release agents, greases, oils, and dirt). Having a lower oil content, the tie-layer has a higher concentration of polymer on the surface, thus, it can form a strong bond with the plastic surface. Since the tie-layer also contains similar chemical constituents as the acoustic transmission gel, it has good compatibility with the gel at the interface. Optionally, the tie-layer may contain additional ingredients that further improve adhesion to the plastic housing, such as adhesion promoters, compatibilizers, coupling agents, and the like.

In another preferred embodiment of the invention, the tie-layer is over-molded by injection molding. A two-stage insert molding process is preferred, wherein the tie-layer is molded first and the acoustic transmission gel is molded second. This process is particularly preferred for large scale manufacturing, wherein high quantities of product are processed. In an alternative embodiment, the adhesive is pre-dissolved in a suitable solvent to reduce its viscosity so it can be applied as a primer onto the plastic housing. In this technique, the solvent is allowed to evaporate before the over-molding with the acoustic thermoplastic transmission gel takes place. This is particularly useful if the production volume is lower. In yet another alternative embodiment, it is possible to cast the thermoplastic gel onto the tie-layer coated plastic housing of the transducer surface, instead of injection molding. In this technique, the thermoplastic gel is heated to above 150° C., preferably above 160° C., and most preferably above 170° C., and then poured onto the plastic housing of the transducer (which was inserted into a mold). At those temperatures the thermoplastic gel is fluid and can be poured with relative ease. The heating temperature is usually kept below 180° C. to prevent excessive fuming. The flash point of the mineral oil which is used as the diluent in the thermoplastic gel is about 220° C.

Commercially available adhesives may also be used in the instant invention (e.g., adhesives such as EC6000 manufactured by ECLECTIC PRODUCTS, INC., Carson, Calif.

90745). Commercially available adhesives can be employed to bond the acoustic transmission gel onto the plastic housing (e.g., EC6000 adhesive can be brushed onto the surface of plastic housing as thin layer prior to the over-molding of the acoustic transmission thermoplastic gel).

In another embodiment of the instant invention, a thermoplastic gel is directly molded onto the transducer, i.e., the piezoelectric acoustic actuator and sensor rather than onto a plastic housing which contains the transducer. The injection or casting temperature of the thermoplastic gel is carefully monitored to prevent damage to the piezoelectric actuator and sensor by the high temperature. If an adhesive or primer is used, it is applied directly onto the surface of the piezoelectric units prior to overmolding.

In another preferred embodiment of the invention, a thermoset gel, such as silicone or polyurethane, is cast onto the ultrasonic transducer. The gel may be cast directly onto the transducer device itself or onto the plastic housing. Thermoset gels are also available through commercial suppliers and are generally provided in a two-part liquid form (i.e., the gel is then mixed in a preset ratio according to the manufacturer's instructions). The thermoset gel mixture is cast around the transducer which is previously put inside a mold prior to casting. The casting is left in the mold and heated to a desired temperature to complete curing of the gel. Silicone gels can be cured at an ambient temperature of about 23 C. for 48 hours, or at 120° C. for 1 hour. For polyurethane gels, the initial curing temperature is 1 hour at ambient temperature of about 23 C., followed by post curing at 100° C. for 16 hours. When using thermoset gels in the instant invention, it is also possible to use an adhesive or a primer to ensure good bonding at the interface. For silicone gels, a RTV silicone adhesive or primer can be employed. For polyurethane gels, a polyurethane based adhesive is preferred. In an alternative embodiment, thermoset gels are applied to the transducer by liquid injection molding. The two gel parts are stored in separate tanks, after which they are pumped into an inline static mixer according to the desired preset ratio. The mixture is then injected into the mold to encapsulate the transducer.

d) Low Frequency Operation

The application of principles of sonar technology to monitor blood flow in accordance with embodiments of the present invention offers the advantage of retaining the full frequency content of the signal received. This is achieved by converting signal received from the moving target (such as flowing blood), into a Doppler shift in frequency.

Specifically, a first piezoelectric device generates an operating (carrier) ultrasound signal at a given frequency. The velocity of the moving material within a subject modulates this carrier frequency, in a manner analogous to conventional frequency modulation technology utilized in an FM radio broadcast. The frequency of the Doppler shift is linearly proportional to the velocity of the moving material within a subject.

A second piezoelectric device picks up the frequency-modulated signal. The Doppler shift frequencies are then converted back to the original signal.

The Doppler effect is employed as a vehicle to transform non-invasively and truthfully, the signal of interest (e.g. blood flow pulses) into a voltage signal. The specific Doppler frequencies received have no bearing on the specific frequency content of the received signal of interest. The Doppler frequencies serve merely as the media for translation of the motion of the blood to an electrical signal, from which heart rate and other vital information can be computed.

In theory, independence of blood flow signal from Doppler frequency and from the operating/carrier frequency should render all operating frequencies suitable for use in accordance with embodiments of the present invention. However, in practice a number of important factors must be considered in selecting an operating/carrier frequency.

Certain factors favor using a high operating/carrier frequency. For example, the wrist offers an relatively accessible and convenient location for positioning the monitoring device. The relatively shallow focal depth of the radial artery in the wrist suggests using ultrasound energy of high frequency suitable for interrogating such shallow focal depths.

The size and weight of the device also favors use of a high operating/carrier frequency. In general, the smaller an electromechanical resonator, the higher its emitted frequency. For a device intended to be worn on the wrist during active physical exercise, the size of the transducer and hence its possible range of output frequency, is limited.

Still other factors favor the use of a low operating/carrier frequency.

For example, electromechanical transducers operating at a high frequency tend to vibrate more rapidly and consume more power than transducers operating at lower frequencies. For a blood flow monitor intended to be worn on the wrist, the available power supplied by a small battery is limited, and transducer actuation at lower frequencies is indicated. The AM or FM amplifier and demodulation circuits in the system will also consume less power at lower operating frequency. In principle, the power consumption is linearly proportional to the operating frequency.

Given at least the above consideration of power consumption, and despite the disadvantages of blood pulse sensing utilizing low carrier/operating frequencies described above, in accordance with certain embodiments of the present invention, it may be valuable to detect blood flow utilizing ultrasound energy having a frequency of 2 MHz or less.

A number of design factors facilitating heart rate monitoring of the radial artery utilizing applied operating/carrier frequencies of 2 MHz or less, have been discovered. These design factors are shown and described below in connection with FIGS. 5A-C.

Figure 5B:
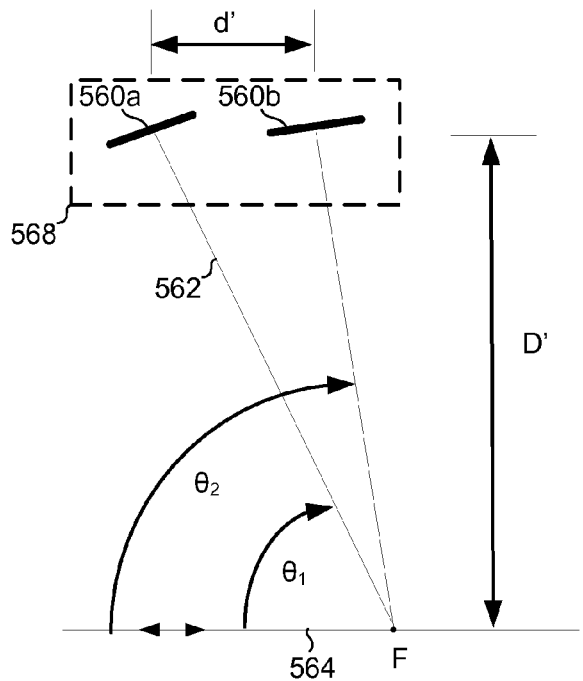
FIGS. 5A-C depict arrangements of two piezoelectric elements in a transducer module.
Figure 5A:
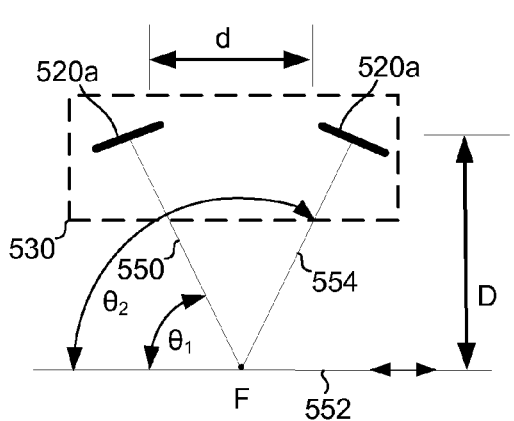

FIG. 5A shows a simplified schematic view of one embodiment of a device for heart rate monitoring in accordance with the present invention. Piezoelectric transducers 520a and 520b are positioned within transducer module 530, separated by a distance d. Piezoelectric transducer 520a emits ultrasound signal 550 at the operating/carrier frequency, to focal point F of vessel 552 having blood flowing therethrough in the directions indicated. Blood vessel 552 is positioned at a focal depth D from transducers 520a-b.

As blood flows through vessel 552 in the directions indicated, movement in the wall of a blood vessel, and in the moving mass of the flowing blood itself, create shifts in the Doppler frequency.

The direction of motion of the blood vessel wall is transverse to the direction of blood flow. The amount of transverse motion of the vessel wall is restricted by its stiffness. Moreover, the resulting acoustic signal is also dampened by surrounding tissues, such that the amplitude and high frequency content of this form of acoustic signal are compromised.

By contrast, the mass of the blood driven through the vessel by blood pressure pulses, moves relatively freely. When the blood cells are free to move through the vessel under this applied pressure, some will travel faster than the others. These faster-moving cells will yield higher Doppler frequencies.

These higher Doppler frequencies can in turn be demodulated into higher voltage signals. Therefore, the demodulated signal has larger amplitude. Since the faster blood cells have high mobility, the demodulated voltage signals presenting them, will also be of high frequency. Since these high frequency signals have higher amplitudes, they have a much better chance at being retained after filtering out of the low frequency noise signals.

Because of this high frequency component of the mass of blood moving through the vessel, even large amplitude, low frequency (<10 Hz) signals induced by muscle motion can be filtered out by a single-stage or a multiple-stage high pass filters in either analog and/or digital form. Heart rate information can thus be effectively obtained from the remaining high frequency content of the blood flow signal.

In order to emphasize the high frequency Doppler shift containing important blood flow information, FIG. 5A shows transducers 520a and 520b oriented at an angle relative to the direction of flow of the blood. Specifically, emitted ultrasound energy signal 550 is incident to vessel 552 at an angle θ1, and Doppler-shifted ultrasound energy signal 554 is reflected from vessel 552 at an angle θ2. This angular orientation of the transducers relative to the direction of movement of blood within the vessel can be expressed as the bias angle:

$$\text{bias angle} = \frac{1}{2}(\theta 2 + \theta 1) \quad (1)$$

Figure 5C:
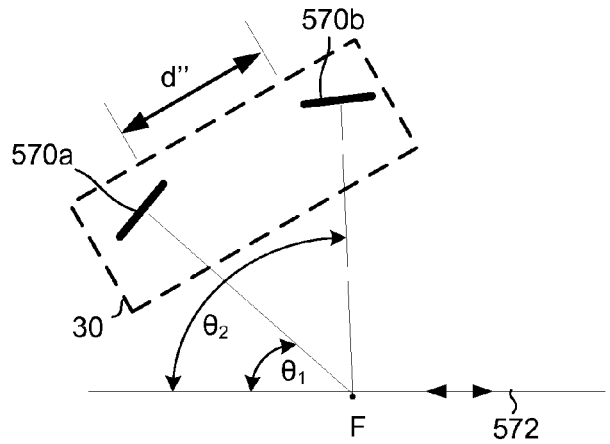

Positioning the two piezoelectric elements of FIGS. 5B-C at a bias angle of less than 90° relative to the direction of blood flow, enhances the Doppler shift in the received signal according to the following equation:

$$F_d = 2F_d V^* \cos \theta / C, \quad (2) \text{ where:}$$

$F_d$=Doppler frequency;
V=flow velocity;
θ=angle of incidence and reflection (θ2=θ1) of energy relative to flow direction; and
C=speed of sound in tissue.

Per Equation (2), exploitation of the bias angle factor enhances the Doppler shift of the received ultrasound signal, according to the component of incident ultrasound energy lying in the same direction as the movement (represented by the cosine). This enhanced Doppler shift increases the signal-to-noise-ratio at the output of the FM detector (or the frequency-to-voltage converter).

Another design factor which can be exploited to optimize sonar detection of blood flow is the orientation of the transducers relative to one another in the module. FIGS. 5A-C also shows transducers 520a and 520b inclined relative to each other by a roof angle:

$$\text{roof angle} = \frac{1}{2}(\theta 2 - \theta 1) \quad (3)$$

The roof angle and distance (d) between the transducers, determines focal depth (D). The larger the roof angle, the shallower the focal depth.

As described above, the bias angle design factor may be exploited to enhance the strength of the signal at the output of the demodulator. By contrast, the roof angle design factor may be exploited to better focus applied ultrasound energy on the shallow radial artery, especially ultrasound energy applied at low operating frequencies.

FIG. 5B shows a simplified schematic view of another embodiment of the present invention, wherein transducer 560a emitting ultrasound energy 562 to vessel 564 positioned at much deeper focal depth D', is inclined at a much smaller roof angle and at a distance (d') relative to second transducer 560b also present within transducer module 568.

Utilizing a large roof angle can allow applied ultrasound energy to be focused at a shallow focal depth, for example as is offered by the radial artery. Such an embodiment is shown in FIG. 5C, wherein transducers 570a and 570b interrogating radial artery 572 positioned at a relatively shallow focal depth are oriented at a large roof angle and separated by a relatively short distance d".

Based on the above, utilizing an appropriate combination of frequency, bias angle, roof angle, and transducer spacing, are each important to determine effectiveness of sonar technology for monitoring heart rate at the radial artery. As the radial artery and hence focal distance (D) typically lies between about 3-10 mm, the roof angle may range from about 0-60°, and preferably between about 5-45°. Under these conditions, the distance between emitting and receiving transducers will lie between about 0.5-20 mm, and preferably between about 1-10 mm.

By virtue of its position between the transducers and the flowing blood, the shape and the thickness of the gel pad can offer additional design parameters to allow apparatuses in accordance with the present invention flexibility in determining bias angle. FIGS. 6A-C depict a number of possible different shapes of gel pads 50, which are designed for a given bias angle and a focal depth.

FIG. 6A shows the gel pad 50 formed in a rectangular shape. FIG. 6B shows the gel pad 50 formed in a wedge shape, and FIG. 6C shows the gel pad 50 formed in a trapezoidal shape. The dimensions of these gel pad shapes are based on the desired bias angle and the depth of the object whose movement is to be detected.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An ultrasonic monitor for measuring pulse rate values in a living subject, comprising:
   a) at least one source of ultrasonic energy;
   b) a gel pad comprised of a thermoplastic elastomer and from about 50 to about 95% by weight of an ultrasound conductive diluent, said gel pad is positioned to be directly between the energy source and the living subject, said gel pad is characterized by having needle penetration from about 5 to about 300 (1/10 mm) according to ASTM D15;
   c) an ultrasonic energy detector;
   d) a microcontroller, responsive to the ultrasonic energy detector, which detects and calculates the pulse rate; and
   e) a display unit, responsive to the microcontroller, which displays a readout of the pulse rate.

2. The ultrasonic monitor of claim 1, wherein:
said gel pad is characterized by having needle penetration from about 25 to about 300.

3. The ultrasonic monitor of claim 1, wherein:
said gel pad is characterized by having needle penetration from about 30 to about 150.

4. The ultrasonic monitor of claim 1, wherein:
said thermoplastic elastomer is a styrene-butadiene-styrene block copolymer.

5. The ultrasonic monitor of claim 1, wherein:
said thermoplastic elastomer is a styrene-isoprene-styrene block copolymer.

6. The ultrasonic monitor of claim 1, wherein:
said thermoplastic elastomer is a styrene/ethylene-co-butylene/styrene block copolymer.

7. The ultrasonic monitor of claim 1, wherein:
said thermoplastic elastomer is a styrene/ethylene-co-propylene/styrene block copolymer.

8. The ultrasonic monitor of claim 1, wherein:
said thermoplastic elastomer is an ethylene/ethylene-co-butylene/ethylene block copolymer.

9. The ultrasonic monitor of claim 1, wherein:
said ultrasound conducting diluent is selected from the group consisting of dibutyl phthalate, dioctyl phthalate, mineral oils, naphthenic oils, paraffinic oils, polybutenes, and vegetable oils.

10. The ultrasonic monitor of claim 1, wherein: said at least one source of ultrasonic energy, said gel pad, said ultrasonic energy detector and said microcontroller are part of a wristwatch assembly.

11. The ultrasonic monitor of claim 1, wherein: the source of ultrasonic energy and the ultrasonic energy detector are located within a first module and communicate by wireless transmission with the display unit.

12. The ultrasonic monitor of claim 11, wherein:
said first module is part of a wristwatch.

13. The ultrasonic monitor of claim 11, wherein: the display unit is housed in a second module.

14. The ultrasonic monitor of claim 13, wherein:
the second module is part of a wristwatch.

15. The ultrasonic monitor of claim 1, wherein: the source of ultrasonic energy and the ultrasonic energy detector are located within a first module and are hardwired to the display unit.

16. The ultrasonic monitor of claim 15, wherein:
said first module is part of a wristwatch.

17. An ultrasonic monitor of claim 1, wherein:
the source of ultrasonic energy and the ultrasonic energy detector are held in place by a head band.

18. The ultrasonic monitor of claim 1, wherein:
the source of ultrasonic energy and the ultrasonic energy detector comprises first and second piezoelectric crystals positioned at an angle to each other, the angle determined based on the distance of the source of ultrasonic energy to a target.

19. The ultrasonic monitor of claim 18, wherein:
the first piezoelectric crystal is energized by an original ultrasound frequency signal;
the original ultrasound frequency signal is reflected off said target and received by the second piezoelectric crystal; and
the received ultrasound frequency signal is higher or lower than said original ultrasound frequency signal depending on direction and speed of fluid flow.

20. The ultrasonic monitor of claim 19, wherein:
the original ultrasonic frequency signal has a frequency of 2 MHz or lower.

21. The ultrasonic monitor of claim 19, wherein:
the first and second piezoelectric crystals are positioned in a wristwatch proximate to a radial artery of a subject.

22. The ultrasonic monitor of claim 19, wherein:
the first and second piezoelectric crystals are positioned proximate to an ulnar artery of a subject.

23. The ultrasonic monitor of claim 19, wherein:
the first and second piezoelectric crystals are inclined at a roof angle relative to each other of between about 0 and 60°.

24. The ultrasonic monitor of claim 19, wherein:
the first and second piezoelectric crystals are inclined at a roof angle relative to each other of between about 5 and 45°.

25. The ultrasonic monitor of claim 19, wherein:
the first and second piezoelectric crystals are separated by a distance of between about 0.5 and 20 mm.

26. The ultrasonic monitor of claim 19, wherein: the first and second piezoelectric crystals are separated by a distance of between about 1.0 and 10 mm.

27. The ultrasonic monitor of claim 1, wherein:
the source of ultrasonic energy and the ultrasonic energy detector are positioned within a module that is inclined relative to a target.

28. The ultrasonic monitor of claim 27, wherein:
an inclination of the module results from an angular shape of the gel pad.

29. The ultrasonic monitor of claim 28, wherein:
the gel pad has a trapezoidal cross-sectional shape.

30. The ultrasonic monitor of claim 28, wherein:
the gel pad has a triangular cross-sectional shape.

31. The ultrasonic monitor of claim 1, wherein:
the hardware comprises a demodulator configured to convert a Doppler shift of a reflected ultrasound energy into a voltage.

32. The ultrasonic monitor of claim 31, wherein:
the demodulator comprises an FM demodulator.

33. The ultrasonic monitor of claim 31, wherein:
the demodulator comprises an AM demodulator.

34. The ultrasonic monitor of claim 31, wherein:
the demodulator comprises an RF mixer or a Gilbert cell.

35. A method for detecting pulse rates in a living subject, comprising:
(i) providing an ultrasonic monitor, said ultrasonic monitor comprises:
a) at least one source of ultrasonic energy,
b) a gel pad comprised of a thermoplastic elastomer and from about 50 to about 95% by weight of an ultrasound conductive diluent, wherein said gel pad is characterized by having needle penetration from about 5 to about 300 (1/10 mm) according to ASTM D15; wherein said gel pad is positioned directly between the energy source and the living subject,
c) an ultrasonic energy detector, and
d) means for detecting and calculating the pulse rate and displaying a readout of the pulse rate; and
(ii) contacting said ultrasonic monitor with the living subject at a point where the pulse rate is to be measured; and
(iii) measuring the pulse rate of the living subject with said ultrasonic monitor contacting the living subject.

36. The method of claim 35, wherein:
said living subject is a human.

37. A method of claim 35, wherein: said contacting includes contacting said ultrasonic monitor to the subject on a radial or ulnar artery.

38. A method of claim 35, wherein: said pulse rate is based on at least one of heart rate, blood flow rate, fetal heart rate, and fetal blood flow rate.

39. The method of claim 35, wherein:
the source of ultrasonic energy and the ultrasonic energy detector are provided in a module, separated by a distance of between about 0.5 and 20 mm and inclined relative to one another at a roof angle of between about 0 and 60°.

40. The method of claim 39, wherein: the module is inclined by resting on an angular shape of the gel pad.

* * * * *